United States Patent
Barakat et al.

(10) Patent No.: US 9,962,410 B2
(45) Date of Patent: May 8, 2018

(54) COMPOSITIONS AND METHODS RELATED TO ORGAN OR TISSUE DECELLULARIZATION

(71) Applicants: Omar Barakat, Houston, TX (US); Jesus Rios, Alvin, TX (US)

(72) Inventors: Omar Barakat, Houston, TX (US); Jesus Rios, Alvin, TX (US)

(*) Notice: Subject to any disclaimer, the term of this patent is extended or adjusted under 35 U.S.C. 154(b) by 103 days.

(21) Appl. No.: 14/634,996

(22) Filed: Mar. 2, 2015

(65) Prior Publication Data

US 2015/0306148 A1    Oct. 29, 2015

Related U.S. Application Data

(63) Continuation-in-part of application No. 14/616,736, filed on Feb. 8, 2015, which is a continuation-in-part of application No. 13/688,999, filed on Nov. 29, 2012, now abandoned.

(51) Int. Cl.
*A01N 1/00*   (2006.01)
*A61K 35/12*  (2015.01)
*A61K 35/407* (2015.01)

(52) U.S. Cl.
CPC .............. *A61K 35/407* (2013.01); *A01N 1/00* (2013.01); *A61K 35/12* (2013.01)

(58) Field of Classification Search
CPC ......... A01N 1/00; A61K 35/407; A61K 35/12
See application file for complete search history.

(56) References Cited

U.S. PATENT DOCUMENTS

2005/0266390 A1* 12/2005 Ueda ...................... A61F 2/062
                                                          435/1.1

OTHER PUBLICATIONS

Sano et al., Towards the creation of decellularized organ constructs using irreversible electroporation and active mechanical perfusion. BioMedical Engineering Online, vol. 9 No. 83 (2010) pp. 1-16.*

* cited by examiner

*Primary Examiner* — Kara Johnson
(74) *Attorney, Agent, or Firm* — Roberts Foster LLP

(57) ABSTRACT

Embodiments include methods for decellularizing an organ or tissue comprising conditioning the organ or tissue to be decellularized by exposing the organ or tissue to electricity, as well as methods of using such decellularized organs or tissues.

17 Claims, 1 Drawing Sheet

COMPOSITIONS AND METHODS RELATED TO ORGAN OR TISSUE DECELLULARIZATION

This application is a continuation-in-part of U.S. patent application Ser. No. 13/688,999 filed Nov. 29, 2012, which is incorporated herein by reference in its entirety.

BACKGROUND

Biologically derived matrices have been developed for tissue engineering and regeneration. The methods developed to date rely on high concentrations of detergents for decellularization, which can corrupt the extracellular matrix and/or lead to an inefficient decellularization process due to excessive washing to remove detergents from the decellularized organ. This disclosure describes additional methods for decellularization and recellularization of organs and tissues.

SUMMARY

Certain embodiments are directed to methods for decellularizing an organ or tissue to produce a decellularized matrix (DM). In certain aspects decellularization comprises conditioning an organ or tissue to be decellularized using an electric current. Once an organ or tissue has been conditioned with electric current the organ or tissue is then subjected to a decellularization process. The organ or tissue can be exposed to an electric current or field for at least 1, 2, 3, 4, 5, 6, 7, 8, 9, 10, 11, 12, 13, 14, 15, 16, 17, 18, 19, 20, or more hours. In certain aspects the organ or tissue is exposed to an electric current or field for at least 1 hour. In a further aspect the organ or tissue is exposed to an electric current or field for at least 10 hours. In still a further aspect the organ or tissue is exposed to an electric current or field for about 16 hours. The electric field can be about 500, 1000, 2000, 3000, 4000, 5000, 8000, 10,000 or more volts/cm. In certain aspects the voltage applied to the organ is 500, 1000, 2000, 3000, 4000, 5000, 8000, 10,000, 15,000, 20,000 volts or more. In certain aspects the voltage applied is 500 volts. In a further aspect the voltage applied is about 4000 volts. The electric current or field can be provided in pulses. In certain aspects electric pulses are provided between 10 to 100 microseconds. In certain aspects the electric field is between about 500 to 5000 volts per meter. In a further aspect 1, 2, 3, 4, 5, 6, 7, 8, 9, 10, 20, 50, to 100 pulses are delivered per second.

Decellularizing the organ or tissue comprises perfusing the organ or tissue with a cell disruption solution. In certain aspects the cell disruption solution is a detergent solution. The detergent solution can be less than or about 20, 15, 10, 5, 1, 0.5, 0.25% detergent. In certain aspects the detergent solution comprises one or more ionic detergent. The ionic detergent can be, but is not limited to sodium dodecyl sulfate (SDS), sodium deoxycholate, or Triton X-200. In certain aspects an ionic detergent is sodium dodecyl sulfate (SDS). In a further aspect a detergent solution can comprise a non-ionic detergent. In certain aspects the non-ionic detergent is triton X-100.

In certain embodiments the methods can further comprise contacting an organ or tissue with a cross-linking agent. In certain aspects a decellularized matrix is contacted with a cross-linking agent. The cross-linking agent can be a chemical or electromagnetic radiation. Cross-linking agents include, but are not limited to formaldehyde, Glutaraldehyde, Genipin, and photo-oxidation. In certain aspects the cross-linking agent is ultra-violet radiation. In a further aspect the cross-linking agent is formaldehyde.

Certain embodiments are directed to a decellularized matrix produced by the methods described herein. In certain aspects the decellularized matrix is a liver decellularized matrix. In certain aspects the decellularized liver matrix is an auxiliary transplant to the patient's liver. In a further aspect the decellularized liver matrix can be recellularized. A recellularized liver matrix can comprise hepatocytes functionally coupled to a decellularized liver matrix. The term "functionally coupled" means that hepatocytes or other cells are adhered to the matrix, directly or indirectly, and perform at least part of their recognized biological function, e.g., peptide secretion, metabolism, protein expression, etc. The methods are not limited to liver and can be used with other organs and tissues such as heart, liver, lungs, skeletal muscles, brain, pancreas, spleen, kidneys, stomach, uterus, and bladder.

A patient with a defective or diseased organ can be treated by providing a decellularized matrix from an appropriate organ or tissue. Certain embodiments are directed to treating patients having a defective or diseased organ. A decellularized matrix can be transplanted, e.g., as an auxiliary transplant, in to a patient or grafted on to a diseased or malfunctioning organ (e.g., heart muscle containing an infarct). In certain aspects a patient has chronic liver disease, cardiomyopathy, diabetes, pulmonary fibrosis, muscular dystrophy, cerebral infarct, kidney failure, or other defect or disease. In certain aspects the decellularized matrix is prepared by using electrical current conditioning. In certain aspects the matrix is recellularized with one or more cells. In certain aspects the decellularized matrix is a liver decellularized matrix that is recellularized with one or more cell types found in the liver. In certain aspects the decellularized matrix is at least partially recellularized in vivo. In other aspects the decellularized matrix is at least partially recellularized in vitro.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
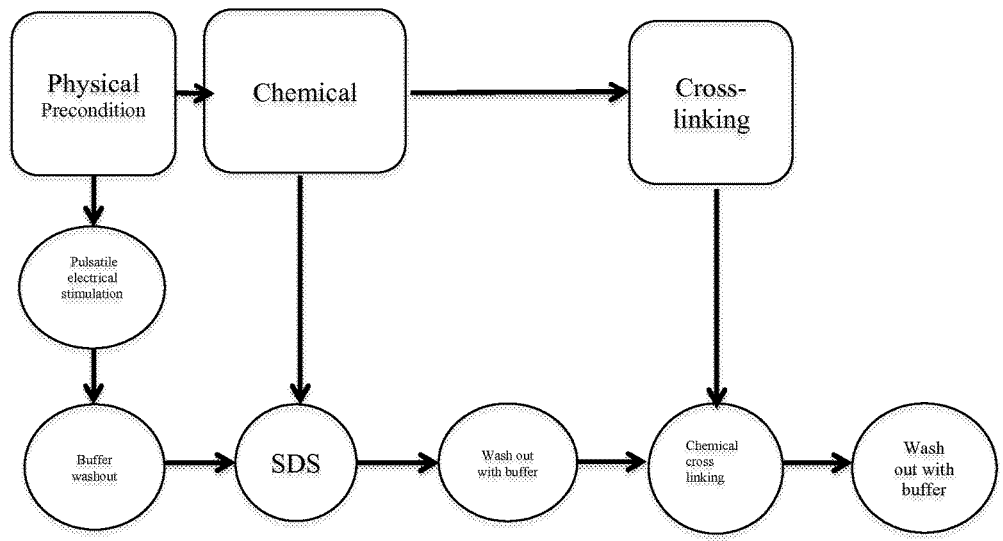
FIG. 1. Flow chart illustrating a protocol for producing decellularized matrices.
Figure 2:
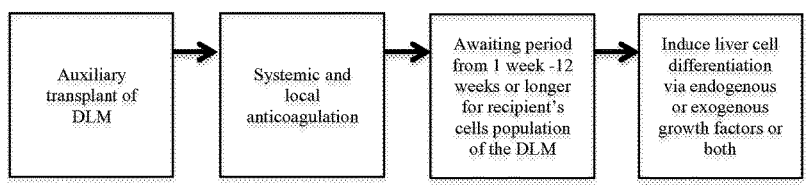
FIG. 2. Flow chart illustrating a protocol for recellularization of decellularized matrix of the liver (DML) in patients with liver disease.

Solid organs generally have three main components, the extracellular matrix (ECM), cells embedded in the ECM, and a vasculature bed. Decellularization of a solid organ as described herein removes most or all of the cellular components while substantially preserving the extracellular matrix (ECM) and the vasculature bed (i.e., a decellularized matrix). A decellularized solid organ then can be used as a scaffold for recellularization. Organs include, but are not limited to those organs obtained from mammals such as rodents, pigs, rabbits, cattle, sheep, dogs, and humans. Types of solid organs as referred to herein include, but are not limited to heart, liver, lungs, skeletal muscles, brain, pancreas, spleen, kidneys, stomach, uterus, and bladder. A solid organ as used herein refers to an organ that has a "substantially closed" vasculature system. A "substantially closed" vasculature system with respect to an organ means that, upon perfusion with a liquid, the majority of the liquid is contained within the solid organ when the major vessels are cannulated, ligated, or otherwise restricted. Despite having a "substantially closed" vasculature system, many of the solid organs listed above have defined "entrance" and "exit" vessel(s) that are useful for introducing and moving the liquid throughout the organ during perfusion.

In certain embodiments, tissues such as skin, or cartilage can be decellularized as described herein.

A decellularized organ or tissue as described herein (e.g., heart or liver) or any portion thereof (e.g., an aortic valve, a mitral valve, a pulmonary valve, a tricuspid valve, a pulmonary vein, a pulmonary artery, coronary vasculature, septum, a right atrium, a left atrium, a right ventricle, a left ventricle or a hepatic lobe), with or without recellularization, can be used for transplanting or grafting into or onto a patient.

Certain embodiments are directed to a decellularization process that includes one or more of the following steps or procedures: (a) conditioning the organ using an electric current, (b) perfusion of the organ with a cellular disruption medium, (c) cross linking the non-cellular components remaining after cellular disruption.

A. Pulsatile Electrical Stimulation (PES)

In certain aspects, the organ or tissue is conditioned using electric current. The organ is harvested and washed. After harvesting the organ is submerged in a conditioning medium. In certain aspects the condition medium comprises an ionic solution that conducts electricity. The electrodes are connected to an electrical pulse generator to provide low energy direct electrical current at a voltage of 100, 200, 300, 400, 500, 600, 700, 800, 900, 1000, 2000, 3000, 4000, 5000, to 20,000 volts or more for 1, 4, 8, 12, 16, 20, to 24 or more hours. The length of the electrical pulses can be set between 20-100 microseconds to generate an electrical field between 500-25000 V/cm. In certain aspects 1 to 10 pulses are delivered per second. In certain aspects the voltage is applied using a Zareba low impedance fence controller (model number EAC50M-Z).

B. Decellularization

The invention provides for methods and materials to decellularize an organ or tissue. After conditioning, an organ is cannulated. The vessels, ducts, and/or cavities of an organ can be cannulated using methods and materials known in the art. The tissue or cannulated organ is perfuse with a cellular disruption medium.

Methods are known in the art for perfusing various organ or tissues. By way of example, the following references describe the perfusion of lung, liver, kidney, brain, and limbs. Van Putte et al., 2002, *Ann. Thorac. Surg.*, 74(3):893-8; den Butter et al., 1995, *Transpl. Int.*, 8:466-71; Firth et al., 1989, *Clin. Sci.* (Loud.), 77(6):657-61; Mazzetti et al., 2004, *Brain Res.*, 999(1):81-90; Wagner et al., 2003, *J. Art Organs*, 6(3):183-91.

One example of perfusion is the Langendorff perfusion of a heart. See, for example, Dehnert, *The Isolated Perfused Warm-Blooded Heart According to Langendorff*, In Methods in Experimental Physiology and Pharmacology: Biological Measurement Techniques V. Biomesstechnik-Verlag March GmbH, West Germany, 1988. Briefly, for Langendorff perfusion, the aorta is cannulated and attached to a reservoir containing cellular disruption medium. A cellular disruption medium can be delivered in a retrograde direction (relative to blood flow in an intact organ) down the aorta either at a constant flow rate delivered, for example, by an infusion or roller pump or by a constant hydrostatic pressure. In both instances, the aortic valves are forced shut and the perfusion fluid is directed into the coronary ostia (thereby perfusing the entire ventricular mass of the heart), which then drains into the right atrium via the coronary sinus. For working mode perfusion, a second cannula is connected to the left atrium and perfusion can be changed from retrograde to antegrade.

One or more cellular disruption media can be used to decellularize an organ or tissue. A cellular disruption medium generally includes an ionic detergent such as sodium dodecyl sulfate (SDS), sodium deoxycholate, or Triton X-200; or non-ionic detergent such as Triton x-100. Other chemical solutions such as alkaline or acidic solutions can be used to solubilize the cytoplasmic components of the cells and disrupts nucleic acids. Hypotonic and hypertonic solutions can be used. Solutions comprising EDTA, EGTA; or enzymes such as trypsin, endonucleases and/or exonucleases can be used to lyse the cells, disrupt cell adhesions to the extracellular matrix, cleave peptide bonds, and catalyze the hydrolysis of nucleic acid.

In certain embodiments, a cannulated organ can be perfused sequentially with two or more cellular disruption media. For example, the first cellular disruption medium can include an anionic detergent such as SDS and the second cellular disruption medium can include an ionic detergent such as Triton X-100. Following perfusion with at least one cellular disruption medium, a cannulated organ or tissue can be perfused, for example, with wash solutions and/or solutions containing one or more enzymes such as those disclosed herein. In certain aspects, the wash solution includes sterile water or Phosphate buffer solution PBS. In a further aspect, the organ can be washed with 1, 2, 3, 4, 5, 6, 7, 8, 9 10, 15, 20 liters or more of wash solution, e.g., PBS.

In certain aspects, the direction of perfusion can be alternated (e.g., antegrade and retrograde) to assist in decellularization of the organ or tissue. Decellularization as described herein essentially decellularizes the organ from the inside out, minimizing damage to the ECM. The perfusion can be carried out under constant pressure between 5-120 mmHg at room temperature.

Decellularization can be conducted at temperatures between 4, 10, 15, 20 to 15, 20, 25, 30, 35, and 40° C., including all temperatures and ranges there between. Depending upon the size and weight of an organ or tissue and the particular detergent(s) and concentration of detergent(s) in the cellular disruption medium, an organ or tissue generally is perfused with cellular disruption medium for about 10, 15, 20, 30, 40, 50, 55, or 60 minutes or hours, including all values and ranges there between. In certain aspects an organ can be perfused for days.

In certain embodiments the decellularized organ is treated with a cross-linking agent. Cross-linking agents include, but are not limited to formaldehyde, glutaraldehyde, genipin, and photo-oxidation. The purpose of the cross-linking agents is to stabilize, sterilize, and/or reduce the antigenicity of the decellularized matrix. Cross-linking can strengthen the matrix, and prevents degradation of the ECM.

One or more agents can be applied in or on a decellularized organ or tissue before or after the cross-linking procedure. Such agents include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ or tissue can be further treated with, for example, irradiation (e.g., UV, gamma) to reduce or eliminate the presence of any type of microorganism remaining on or in a decellularized organ or tissue.

C. Recellularization of Organs or Tissues

In certain embodiments a decellularized matrix can be recellularized in vitro or in vivo. An organ or tissue can be recellularized by seeding a decellularized matrix with a population of regenerative cells. Regenerative cells as used herein are any cells that cause or assist in the recellularization of a decellularized organ or tissue. Regenerative cells can be totipotent cells, pluripotent cells, or multipotent cells. Regenerative cells can be autologous or allogenic. In addition, regenerative cells can be undifferentiated cells, partially differentiated cells, or fully differentiated cells.

Regenerative cells as used herein include embryonic stem cells as defined by the National Institute of Health (NIH), fetal cells, inducible pluripotent stem cells, adult-derived stem cells/progenitor cells or mesenchymal stem cells. Cells can be harvested from organs or tissue such as adipose tissue, peripheral blood, umbilical cord blood cells, bone marrow, liver, heart, lung, and pancreas. These cells can be autologous or allogenic. In a certain aspect, the cells are expanded to provide a number that more efficiently builds an organ. Other sources to rebuild an organ would also include tissue or organ derived adult cells such as hepatocytes and pancreatic islet cells. In certain aspects, large numbers of these cells can be harvested prior to implantation in the matrix if the cells have a limited capability to expand prior to recellularization. In certain aspects autologous endothelial cells can be used to re-endothelialize the decellularize organ following transplantation. This will avoid exposure to the recipient's immune response.

The peripheral blood remains a source of stem cells to populate the decellularized matrix following transplantation. These stem cells can be induced in vivo to differentiate into organ-specific cells after they infiltrate the decellularized organ. In certain aspects a systemic and/or local anticoagulation can be used to prevent clotting of the decellularized organ during in-vivo perfusion.

Examples of regenerative cells that can be used to recellularize an organ or tissue includes, but is not limited to embryonic stem cells, umbilical cord blood cells, tissue-derived stem or progenitor cells, bone marrow-derived stem or progenitor cells, blood-derived stem or progenitor cells, adipose tissue-derived stem or progenitor cells, mesenchymal stem cells (MSC), skeletal muscle-derived cells, or multipotent adult progenitor cells (MAPC). Additional regenerative cells that can be used include tissue-specific stem cells including liver-mesenchymal stem cells, cardiac stem cells (CSC), multipotent adult cardiac-derived stem cells, cardiac fibroblasts, cardiac microvasculature endothelial cells, or aortic endothelial cells. Bone marrow-derived stem cells such as bone marrow mononuclear cells (BM-MNC), endothelial or vascular stem or progenitor cells, and peripheral blood-derived stem cells such as endothelial progenitor cells (EPC) or mononuclear-derived multipotential cells (MOMC) also can be used as regenerative cells.

The number of regenerative cells that is introduced into and/or onto a decellularized organ in order to generate an organ or tissue is dependent on both the organ type (e.g., heart and lung require a functional whole organ compared to liver and pancreas which require lesser percentage of their original volume), the size and weight of the organ or tissue, the size and weight of the recipient, and the type and developmental stage of the regenerative cells. Different types of cells may have different tendencies as to the population density those cells will reach. Similarly, different organ or tissues may be recellularized at different densities. By way of example, a decellularized organ or tissue can be "seeded" with at least about 1,000 (e.g., at least 10,000, 100,000, 1,000,000, 10,000,000, or 100,000,000, to 300, 000,000,000 regenerative cells); or can have from about 1,000 cells/mg tissue (wet weight, i.e., prior to decellularization) to about 10,000,000 cells/mg tissue (wet weight) attached thereto.

Regenerative cells can be introduced ("seeded") into a decellularized matrix by injection into one or more locations. In addition, more than one type of cell can be co-cultured together (i.e., a cocktail of cells) in a decellularized organ or tissue. For example, a cocktail of cells can be injected at multiple positions in a decellularized organ or tissue or different cell types can be injected into different portions of a decellularized organ or tissue. Alternatively, or in addition to injection, regenerative cells or a cocktail of cells can be introduced by perfusion into a decellularized organ or tissue. For example, regenerative cells can be perfused into a decellularized organ using a perfusion medium, which can then be changed to an expansion and/or differentiation medium to induce growth and/or differentiation of the regenerative cells. In certain aspects, the decellularized organ can be perfused with blood from a subject scheduled to receive or has received the decellularized organ.

During recellularization, a decellularized matrix is maintained under conditions in which at least some of the regenerative cells can multiply and/or differentiate within and on the decellularized organ or tissue. Conditions include, but are not limited to the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized matrix and the regenerative cells attached thereto are maintained in a suitable environment. For example, the regenerative cells may require a nutritional supplement (e.g., nutrients and/or a carbon source such as glucose), exogenous hormones or growth factors, and/or a particular pH.

Regenerative cells can be allogeneic to a decellularized matrix (e.g., a human decellularized organ or tissue seeded with human regenerative cells), or regenerative cells can be xenogeneic to a decellularized matrix (e.g., a pig decellularized matrix seeded with human regenerative cells). "Allogeneic" as used herein refers to cells obtained from the same species as that from which the organ or tissue originated (e.g., self (i.e., autologous) or non-self (i.e., heterologous) individuals), while "xenogeneic" refers to cells obtained from a species different than that from which the organ or tissue originated.

In some instances, a decellularized matrix or a recellularized matrix generated by the methods described herein is to be transplanted into a patient or grafted onto a patient or patient organ. In those cases, the regenerative cells used to recellularize a decellularized matrix can be obtained from the patient such that the regenerative cells are "autologous" to the patient. Regenerative cells from a patient can be obtained from, for example, blood, bone marrow, tissues, or organs at different stages of life (e.g., prenatally, neonatally or perinatally, during adolescence, or as an adult) using methods known in the art. Alternatively, regenerative cells used to recellularize a decellularized matrix can be syngeneic (i.e., from an identical twin) to the patient, regenerative cells can be human lymphocyte antigen (HLA)-matched cells from, for example, a relative of the patient or an HLA-matched individual unrelated to the patient, or regenerative cells can be allogeneic to the patient from, for example, a non-HLA-matched donor.

Irrespective of the source of the regenerative cells (e.g., autologous or not), the decellularized matrix can be autologous, allogeneic or xenogeneic to a patient.

In certain instances, a decellularized matrix may be recellularized with cells in vivo (e.g., after the decellularized matrix has been transplanted into an individual). In vivo recellularization may be performed as described above (e.g., injection and/or perfusion) with, for example, any of the regenerative cells described herein. Alternatively or additionally, in vivo seeding of a decellularized matrix with endogenous regenerative cells may occur naturally or be mediated by factors delivered to the tissue or organ to be recellularized. These cells will then differentiate into organ specific cells by external delivery of growth factors or by procedure that induce the release of endogenous growth factors. Such procedure may include partial removal of the recipient's liver after implantation of a decellularized matrix, for example. In certain aspects prior systemic and/or local anticoagulation can be administered to prevent clotting of the decellularized matrix.

The progress of regenerative cells can be monitored during recellularization. For example, the number of cells on or in an organ or tissue can be evaluated by taking a biopsy at one or more time points during recellularization. In addition, evaluating markers present in a cell or a population of cells can be used to monitor differentiation of regenerative cells. Markers associated with different cells types and different stages of differentiation for those cell types are known in the art, and can be readily detected using antibodies and standard immunoassays. See, for example, *Current Protocols in Immunology*, 2005, Coligan et al., Eds., John Wiley & Sons, Chapters 3 and 11. Functional analysis of recellularized organs can be conducted. For example, contractions and ventricular pressure can be evaluated in a recellularized heart; albumin production, urea production, and cytochrome p450 activity can be evaluated in a recellularized liver; blood or media filtration and urine production can be evaluated in a recellularized kidney; blood, glucose and insulin can be evaluated in a recellularized pancreas; force generation or response to stimulation can be evaluated in a recellularized muscle; and thrombogenicity can be evaluated in a recellularized vessel.

II. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Decellularization in Combination with Electrical Conditioning

One goal of the decellularization process is to remove the nuclear material with minimal disruption of the extracellular matrix (ECM). The ECM maintains all or part of the biological and mechanical properties of the matrix. This provides an environment supporting the implantation of host cells. The current use of physical methods such as freezing and thawing, followed by perfusion of the organ with chemical detergent and enzymes such as sodium dodecyl sulfate, Triton-X, and Trypsin, for example, disrupt the cell membrane and release cellular content to be washed away. However, Freezing and thawing, and prolong exposure of these organs to commonly used chemical detergents and enzymes is harmful to the ultrastructure and composition of the extracellular matrix. Preconditioning of the mammalian organs with electrical stimulation disrupts the cellular membrane and the tight junction between the cells with no effect on the ultrastructure of the extracellular matrix. The inventor is able to decellularize organs and tissues effectively minimal detergent concentrations. Using electrical conditioning accomplishes the decellularization process in a significantly shorter period of time when compared to other published protocols. Cells can be removed with preservation of the ultrastructure of the ECM.

Preservation of the ECM ultrastructure was confirmed on the post-decellularization examination using electron microscopy, immunohistochemistry, and measurement of the tensile strength of the decellularized matrix. In addition, quantitative measurement of the matrix collagen, elastin, and glycosaminoglycan showed higher concentration of the abovementioned proteins compared with the standard techniques (Table 1). Table 1 demonstrates the difference of decellularization parameters between livers conditioned with electrical stimulation (Group I) and livers not conditioned with electrical stimulation. Following recellularization the cells demonstrated longer survival and better functionality compared with the non-conditioned matrices.

Unmodified decellularized matrices when implanted into a recipient will elicit a specific response with mononuclear cell infiltration that leads to degradation of the matrix and deposition of new host derived ECM in an attempt to remodel the matrix. Matrices that are exposed to collagenase demonstrate significant loss of their mass indicating their susceptibility to enzymatic remodeling compared to matrices that are cross linked. Although, this response is desirable for particular tissues, it may not be beneficial for large vascular organs, as in vivo perfusion of these organs will lead to disintegration and loss of the organ. It has been shown that matrices that were cross-linked maintained their mass compared to the non-cross linked matrices. Cross-linking the collagen fibers using the method described herein provided greater strength of the matrices and maintained their shape and size when perfused in vitro and in-vivo for more than one week compared to the matrices that were not cross linked.

TABLE 1

Comparison between decellularized organs condition using electrical stimulation and organs not conditioned using electrical stimulation.

|  | Group I Electrical Stimulation (ES) | Group II no ES |
|---|---|---|
| Weight of the fresh organ (g) | 313 ± 84 | 263 ± 17.7 |
| Size of the fresh organ (cm) | 16 × 10.3 × 4 | 15 × 9 × 4 |
| Amount of SDS used (L) | 31.6 ± 5.5 | 56.6 ± 4.4 |
| Time to decellularization (min) | 35.3 ± 6.4 | 73 ± 5.5 |
| Degree of the decellularization (%) | 95.6 ± 1.5 | 93 ± 2.4 |
| Weight of the decellularized matrix (DM) (g) | 183 ± 24.2 | 120 ± 6.6 |
| Size of the DM (cm) | 14 × 9.3 × 3 | 12 × 7 × 3 |
| Quantitative level of collagen (% of dry weight) | 8.3 ± 0.4 | 5.6 ± 0.4 |
| Quantitative level of elastin (% of dry weight) | 18 ± 2 | 10 ± 1 |
| Quantitative level of s GAG (% of dry weight) | 0.46 ± 0.1 | 0.2 ± 0.06 |
| Level of animal DNA left (%) | 3.5 + 1.5 | 6.6 + 2.4 |

The invention claimed is:

1. A method for decellularizing an organ comprising:
   (a) preconditioning the organ prior to decellularization by exposing the whole organ to a pulsatile electric stimulation, wherein said organ, and electrodes are submerged in a conditioning medium; and
   (b) after 4-8 hours following exposure to the pulsatile electric stimulation, the organ is perfused with a washing solution to wash cellular debris from the organ.

2. The method of claim 1, wherein the organ is exposed to the pulsatile electric stimulation for at least 1 hour.

3. The method of claim 1, wherein the organ is exposed to the pulsatile electric stimulation for at least 10 hours.

4. The method of claim 1, wherein the organ is exposed to the pulsatile electric stimulation for 16 or 24 hours.

5. The method of claim 1, wherein the washing solution is water.

6. The method of claim 1, wherein the washing solution is a cell disruption solution.

7. The method of claim 6, wherein the cell disruption solution is a detergent solution.

8. The method of claim 7, wherein the detergent solution is less than 5% detergent.

9. The method of claim 7, wherein the detergent solution is less than 0.25% detergent.

10. The method of claim 7, wherein the detergent solution comprises an ionic detergent.

11. The method of claim 10, wherein the ionic detergent is sodium dodecyl sulfate (SDS), sodium deoxycholate, or sodium 2-[4-(1,1,3,3-tetramethylbutyl)phenoxy]ethyl sulfate.

12. The method of claim 7, wherein the detergent solution comprises a non-ionic detergent.

13. The method of claim 12, wherein the non-ionic detergent is polyethylene glycol p-(1,1,3,3-tetramethylbutyl)-phenyl ether.

14. The method of claim 1, further comprising exposing the decellularized organ to a cross-linking agent.

15. The method of claim 1, wherein the organ is liver, heart, or kidney.

16. The method according to claim 1, wherein following said preconditioning, said organ is cannulated.

17. The method according to claim 1, wherein said pulsatile electrical stimulation comprises pulses between 20-100 microseconds to generate an electrical field between 500-25000 V/cm.

* * * * *